(12) United States Patent
Reszka et al.

(10) Patent No.: US 7,462,703 B2
(45) Date of Patent: Dec. 9, 2008

(54) AGENT FOR GENE TRANSFER

(75) Inventors: Regina Reszka, Schwanebeck (DE); Antje Berndt, Zepernick (DE)

(73) Assignee: Max-Delbruck-Centrum fur Molekulare Medizin, Berlin (DE)

( * ) Notice: Subject to any disclaimer, the term of this patent is extended or adjusted under 35 U.S.C. 154(b) by 0 days.

(21) Appl. No.: 10/355,933

(22) Filed: Jan. 31, 2003

(65) Prior Publication Data

US 2004/0152647 A1   Aug. 5, 2004

(51) Int. Cl.
*C07H 21/04* (2006.01)
*A61K 31/70* (2006.01)
*A61B 5/055* (2006.01)

(52) U.S. Cl. .................. 536/23.1; 514/44; 424/9.321

(58) Field of Classification Search ............... 536/23.1, 536/24.5
See application file for complete search history.

(56) References Cited

U.S. PATENT DOCUMENTS

| | | | |
|---|---|---|---|
| 5,542,935 A * | 8/1996 | Unger et al. ................. 604/190 |
| 5,654,185 A * | 8/1997 | Palsson .................... 435/235.1 |
| 6,207,133 B1 * | 3/2001 | Reszka et al. ............. 424/9.321 |
| 6,245,318 B1 * | 6/2001 | Klibanov et al. ........... 424/9.52 |
| 6,479,033 B1 * | 11/2002 | Reszka et al. .............. 424/9.32 |

FOREIGN PATENT DOCUMENTS

WO    WO 9427580 A1 * 12/1994
WO    WO 9614864 A1 *  5/1996

OTHER PUBLICATIONS

Definition of "cytostatic" printed from Answers.com.*

* cited by examiner

*Primary Examiner*—Tracy Vivlemore

(57) ABSTRACT

An agent for the transfer of genetic material comprising a genetic material, PEG-containing liposomes, one or more additional polymer particles and a contrasting agent. The invention also is directed toward methods of preparing the agent, and methods of using the agent to affect gene transfer.

28 Claims, 2 Drawing Sheets

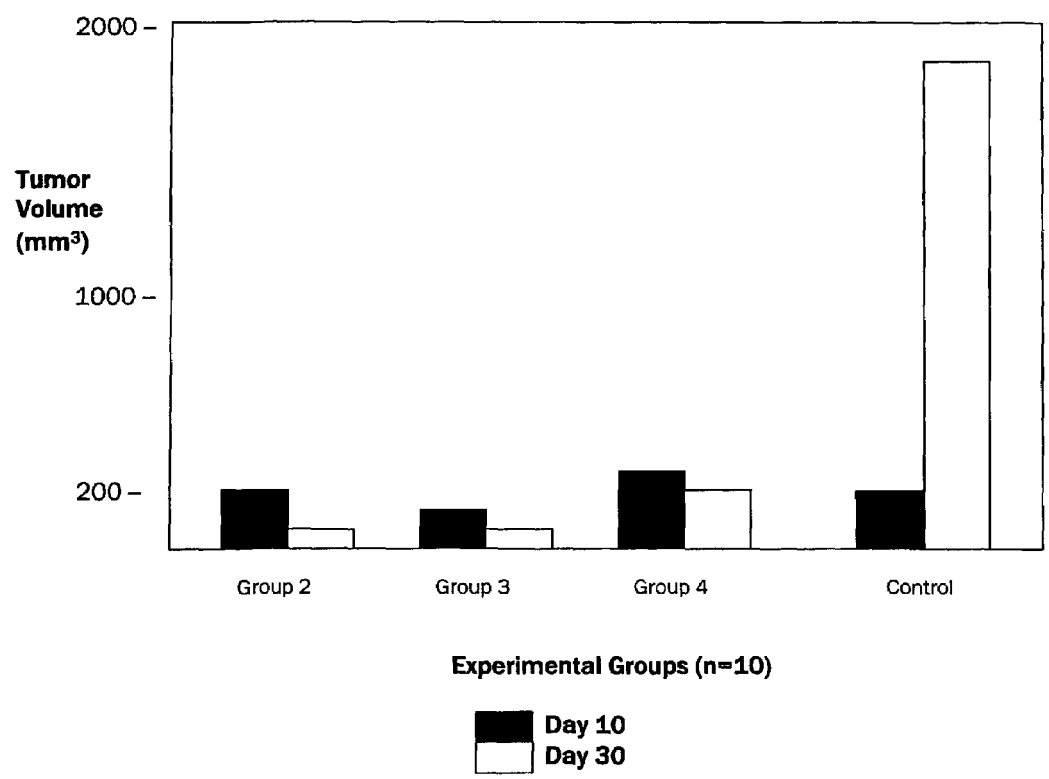
Fig. 1 Average Tumor Volume Before and After Gene Therapy

Fig. 2 Major Arteries Involved in Administering the Gene Transfer Agent
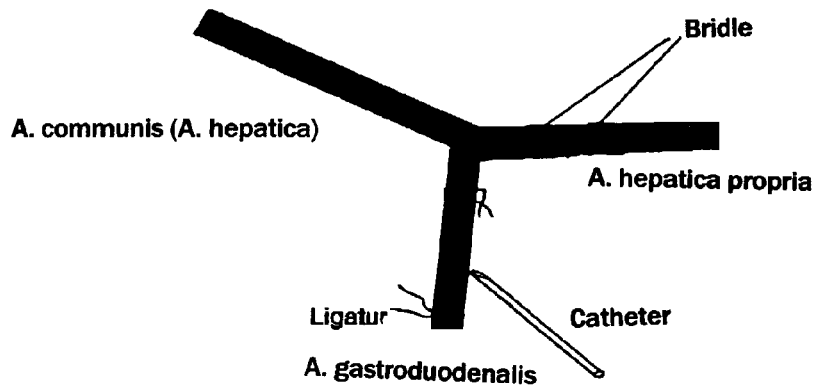

AGENT FOR GENE TRANSFER

BACKGROUND OF THE INVENTION

The invention relates to an agent for the gene therapy of tumor diseases and neurodegenerative, cardiovascular and autoimmune diseases. Areas of application for the invention are medicine and the pharmaceutical industry.

After bronchial carcinoma in men and breast tumors in women, tumors of the large intestine and the colon are the malignant tumors, which occur most frequently in Germany. For these patients, the essential therapeutic measure consists of the radical resection of the tumor-carrying section of the intestine. However, metastasizing (primarily liver metastasizing) is the main cause of the high mortality of colorectal carcinoma. When surgical treatment of the metastases no longer is possible, intensive chemotherapy generally remains the last means of choice.

In spite of intensive research of new potent chemotherapeutic agents, the treatment of tumors that cannot be resected, especially of liver metastases, continues to be a problem because colorectal carcinoma have a low cell proliferation rate, a tumor heterogeneity and a resistance to drugs. A different reason for the frequent failure of chemotherapy lies therein that the cytostatic agents, presently available, do not attack certain metabolic paths of tumors selectively nor are directed exclusively against tumor cells. Consequently, the use of cytostatic agents is associated with many severe side effects.

The use of liposomes and polymers offers the possibility of modifying the pharmacological properties of chemotherapeutic agents.

In spite of decades of intensive efforts to heal patients with inoperable tumors with the help of chemotherapy, progress must be described as slight. With the exception of a few diseases (such as acute lymphatic leukemia) complete healing of the patients by chemotherapeutic measures alone is not possible. In many cases, no significant increase in the life expectancy can be detected. This is due, on the one hand, to the slight tumor specificity of many chemotherapeutic agents and, on the other, to the relatively high toxicity of these substances. Consequently, in spite of massive side effects, an adequate activity level can be observed only rarely in the tumor. In 28 different studies, a total of 663 patients were treated with 22 different substances. Only six patients showed a complete tumor regression and 63 a temporary one which, however, in most cases did not lead to a significant prolongation in the survival time. These studies confirm clearly the need for improving existing therapy concepts and, optionally, for developing new starting points.

Because of their similarity to cell membranes, liposomes have been used for 23 years as multifunctional carrier and transporting systems for biologically active substances, including prokaryontic and eukaryontic genes (Kim, S., Drugs, 1993, 46: 618-638). They can be characterized as closed microscopic structures, which consist of concentrically disposed lipid double layers, which in turn separate aqueous compartments from one another. Particularly extensive is the work dealing with the liposomal encapsulation of medicinal drugs. In comparison to other carrier systems, the liposomes offer the advantage here that they can be utilized also for the encapsulation of DNA constructs.

The ability to select the composition, charge, size and stability, depending upon the problem that is to be solved.

The possibility of complete biological degradation.

The practical absence of immunological and toxic reactions.

The frequently changed pharmacokinetics of the liposomally encapsulated substance.

The changed organ distribution and tropism to certain organs.

The possibilities for different methods of targeting (antibodies, lectins)

Liposomes can also be used as gene-transfer systems.

However, in the majority of animal experimental models, the gene transfer was carried out ex vivo. The knowledge concerning a tumor-specific immune response, induced by the gene-modified tumor cells and obtained by these means, has led to the strategy of a "vaccination" with cytokinin-gene transfected tumor cells. An in vivo gene transfer strategy was employed within the scope of an RAC-approved study at the University of Michigan Medical Center, Ann Arbor. The transfer of an MHC class I (HLA-B7) gene into the tumor cells was to be achieved by the direct injection of liposomes/plasmid DNA complexes into the tumor tissue, in order to stimulate an immune reaction by these means. Other gene transfer systems make use of suicides genes, in order to make tumor cells sensitive to chemotherapeutic substances. Different genes, which can cause a selective killing of the expressed cells, have been tested for this purpose.

A simple and, according to first clinical data, also effective system was developed by K. Culver (Culver, K. W. et al., Science 1992, 256: 1550) and has already been employed in clinical studies. The strategy is based on the transfer of the herpes simplex thymidine kinase (HSV-tk) gene into tumor cells by means of a retroviral vector. HSV-tk-transfected cells become sensitive to the anti-virus substance ganciclovir. Due to HSV-tk, ganciclovir becomes a nucleotide-like precursor which, after further phosphorylization, is incorporated into the DNA-dividing cells and leads to a stop in the symphysis of DNA and to the death of the cell.

By means of an adaptation of the Culver suicide strategy to the liver metastasis model and after injection of HSV-tk vector-producing cells, Caruso et al. (Proc. natl. Acad. Sci., 1993, 90: 7024-7028) was able to confirm a regression of established, macroscopically visible liver metastases. However, it is a disadvantage of this application of a tumor therapy with viral vectors that, because of the immunological defense mechanism of the organism, only a single administration of the gene vector construct is possible. For a liposomal vector, repeated systemic processing is possible.

For the treatment of tumors, the access to which is relatively difficult (such as multiple liver metastases, brain tumors), the selective and safe application and transfection with retroviral or adenoviral vectors still is a problem, quite apart from the treatment risks, which occur with viral infections. As little as possible of healthy tissue should be destroyed and involved, while the transfer efficiency is as high as possible and the subsequent tumor regression is complete.

Until now, no liposomally packaged therapy gene or suicide gene has been transfected in liver metastases at the CC531 carcinoma.

BRIEF SUMMARY OF THE INVENTION

It is an object of the invention to supply completely new starting points for a loco-regional treatment of tumors, especially of liver metastases, by a combined use of liposomes/plasmid DNA complexes of different composition, size and loading.

The object of the invention is accomplished by the distinguishing features described in the present claims.

The core of the invention is a pharmaceutical agent comprising one one or more genetic materials, not encapsulated or encapsulated in PEG-, immuno-, immuno/PEG-, cationic, optionally polymer-modified liposomes, lyophilized or degradable starch particles and/or gelatin and/or polymer particles, such as nanoparticles and iodine-, gadolinium-, magnetite- or fluorine-containing contrasting agents.

Genetic materials preferably are DNA, RNA, ribozyme, antisense oligonucleotides and, especially preferably, therapy genes, such as suicide genes, cytokin genes, chemokin genes (MIP1α, MCP), antiangiogenesis genes, such as vascular endothelial growth factor (VEGF), apoptose genes, such as apoptin, natural born killer (NbK), optionally in combination with marker genes, such as green fluorescence protein (GFP), galactosidase gene (LacZ) under optionally inducible, optionally tissue-specific promoters.

A further variation of the agent consists therein, that it additionally contains the proteins, which pack DNA more tightly, such as nuclear capsid protein (NCP 7), HMG and/or synthetic substances, such as polyethylene imine, poly-L-lysine or protamine sulfate.

Preferred suicide genes are herpes simplex virus thymidine kinase gene (HSVtk), deaminase gene, NR/CB1954, pyrine nycleoside phosphorylase and/or the cytokinin genes IL-2, IL-4, IL-6, IL-10, IL-12 and/or IL-15.

The liposomes consist of a) a natural, semi-synthetic or completely synthetic amphiphile b) a steroid, c) a charged lipid component, d) the water- or lipid-soluble genetic material and/or e) a carrier liquid and optionally additional inert materials.

The quantitative ratio of a to b to c preferably is in the molar ratio of 1:0.3:0.1 to 1:1:0.1 or 1:1:0.5 and the molar ratio of c to d is 2:1 to 10:1.

The natural, semi-synthetic or fully synthetic amphiphile preferably is a lipid, a surfactant, an emulsifier, polyethylene glycol (PEG) or lipid-PEG, the amphiphile being a compound of the general formula I

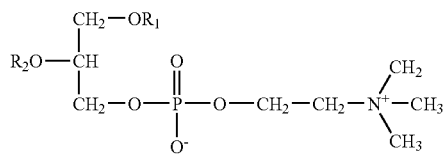

(I)

in which $R_1$ and $R_2$ represent $C_{10}$ to $C_{20}$ alkanoyl, alkenoyl, alkyl or alkenyl.

The steroid used is cholesterol, diethoxycholesterol or sitosterol.

The charged lipid component is the anion of diacetyl phosphate, of palmitic acid or of stearic acid, the anion of a phospholipid, such as phosphatidyl serine, phosphatid acid or the anion of a sphingolipid, such as sulfatid, or polyethylene glycol (PEG), such as MPEG-DSPE.

A preferred embodiment of the agent consists therein that the charged lipid component is fluorinated.

Furthermore, as additional inert materials, polymer particles in the form of a 25% aqueous solution of Poloxamer can be used.

Preferably, the genetic materials are present in

SUV (small unilamellar vesicles) PEG liposomes,

LUV (large unilamellar vesicles) PEG liposomes,

REV (reverse phase evaporation vesicles) PEG liposomes,

MLV (multilamellar vesicles) PEG liposomes, anti-Ki-67-immune PEG liposomes, anti-CEA PEG liposomes or PEG DAC-Chol liposomes.

On the average, the starch particles, preferably lyophilized, are present in a size of 40-90 μm and are in a physiological salt solution in a concentration of 5 to 70 mg/mL. It is especially preferred if the starch particles have a particles size of 60 to 90 μm.

The inventive agent contains, as iodine-containing contrasting agent, phenyl derivatives with one or more iodine substituents, such as preferably Iopromide, Ioxitalamate, Ioxaglate, Iopamidol, Iohexyl, Iotralon, Metrizamide or Ultravis.

Fluorinated lipids also come into consideration as contrasting agents.

A very suitable embodiment is an agent, which contains 30 to 90 mg of lyophilized or degradable starch particles and 5 to 100 mg of genetic material, which is or is not encapsulated.

A particularly preferred embodiment of the agent is characterized in that it contains the LacZ marker gene and the pUT HSVtk suicide gene, encapsulated in MLV PEG, as starch particles, Spherex or Gelfoam and a fluorinated contrasting agent.

The agents are prepared in that 30 to 90 mg of the lyophilized or degradable starch particles and/or gelatin and/or polymer particles are dissolved in 3 to 6 mL of contrasting agent and afterwards the therapeutically necessary amount of a genetic material is added.

Preferably, the therapeutic amount of a genetic material and optionally a complexing agent is dissolved in one or several lipids and treated with starch particles and a contrasting agent.

The inventive agent is used for gene transfer and gene therapy, especially for the therapy of liver metastases, tumors of the lung, bladder, head and neck, urogenitals, lymph nodes, breasts, and in the case of glioblastomata, arthritis and asthma.

It can equally well be used for local gene therapy.

In particular, the agent is used for the intraarterial therapy of liver metastases, pancreatic tumors, metastases in the pelvis, for the treatment of neurodegenerative and autoimmune diseases, for Parkinson's and Alzheimer's diseases and for multiple sclerosis, in the case of diabetes type I, to accompany transplantations, for the treatment of restenosis and for high blood pressure.

In summarizing, it is noted once again that the following relationships are of decisive importance for the effectiveness of the inventive liposomes/plasmid DNA complexes.

1. The use of the arterial embolization therapy: (direct access to the tumor supply (75-90%), high local tumor concentration and low systemic toxicity)

2. The combined use of DNA-carrying liposomes with the embolisate (triple carrier system)

3. The use of an effective (strong) promoter.

It should be emphasized as a special advantage that the organism shows hardly any immunological reaction when this liposome/plasmid DNA complex is used (the unlimited, repeated use is possible); moreover, it was not possible to detect any toxicity.

The invention will be described in the following by means of examples.

BRIEF DESCRIPTION OF THE DRAWINGS

FIG. 1. The graph demonstrates the effect of the gene therapy method of the application, on tumor volume at 30 days after tumor inoculation. See text for details.

FIG. 2 The diagram illustrates the major arteries involved in the gene therapy method of the application, and their anatomical relationships.

DETAILED DESCRIPTION OF THE INVENTION

Method:

The In Vivo Investigation for the Treatment of Liver Metastases in the Animal Model.

Multi-lamellar polyethylene glycol liposomes (MLV PEG liposomes) are charged with DNA (suicide gene) and, together with the drug carrier embolization system (DCES), are used intraarterially for the treatment of liver metastases in rats.

Animals:

For the animal investigations, male Wag/Rij rats where used (bred by: Harlan Winkelmann GmbH, Gartenstrasses 27, D-33178 Borchen). The average weight of the animals is 250-280 g. The animals are kept in accordance with the guidelines of the Animal Protection Law, that is, the specifically pathogen-free (SPF) rats are kept under standardized environmental conditions in the trans-genetic tract of the animal laboratory of the Max-Delbrück center, Berlin-Buch. In the animal cages, the temperature is 22° C. (±1° C.), the relative humidity is 50% (±10%) and the light-dark rhythm is 6 a.m. to 6 p.m.) changed every 12 hours. In a standardized cage (type 3), with a bottom area of 810 cm$^2$ and a height of 19 cm, the rats are kept in pairs on a litter of wood shavings (autoclaved at 121° C. for 12 minutes). As standard feed, the animals receive the experimental diet for rats of Firma Sniff, as well as water ad libitum.

Cell Culture:

The CC531 cell line is cultured in an RPMI 1640 medium. The medium contains 10% fetal calf serum, 100 U/mL of penicillin G, 100 μg/mL of streptomycin sulfate and 0.25 μg of amphoterizine. The cells are incubated in the incubator at 5% carbon dioxide, 95% relative humidity and a temperature of 37 C.

Preparation of the Liposomes:

Hydrogenated soybean phosphatidyl choline, cholesterol and polyethylene glycol are dissolved in chloroform in a molar ratio of 1:1:0.1. In the rotary evaporator, the chloroform is evaporated completely from this solution and a lipid film is formed. The lipid film is incubated with distilled water for 12 hours with shaking. During the shaking, MLV PEG liposomes are formed. For preparing the liposomes/DNA complex, the desired concentration of DNA is added to the distilled water phase and shaken with the lipid film as described. At the same time, the DNA is deposited between the lipid double layers that are being formed.

DNA Used:

| Reporter gene | codes the *E. coli* lacZ gene (beta-galactosidase), CMV promoter |
| --- | --- |
| Suicide gene pUT 649 | codes the herpes simplex virus thymidine kinase, CMV promoter |
| Suicide gene pBS CEA-tk | codes the herpes simplex virus thymidine kinase, CEA promoter |

Preparation and Anesthesia of the Experimental Animals

The rats are anesthetized for all experimental work. For this purpose, they are placed for about 30 seconds in an ether pot, from which they are removed when immobilization sets in. The injection anesthesias are applied i.m. (into the muscle of the thigh) by means of a 1 mL mixed injection. The further treatment was continued only after the anesthetic and analgesic effect had set in completely after (about 10 minutes).

| Narcotics | Dose |
| --- | --- |
| 1. Xylazin (Rompun ®, 2%, Bayer AG, Leverkusen | 12 mg/kg KGW |
| 2. Ketamine hydrochloride (Ketanest ®, 50 mg/mL, PARKE-DAVIS GmbH, Berlin) | 80 mg/kg KGW |

For surgical interventions, the hair on the abdomen was shaved by machine. At the shaved area, the tied up and fixed animals were cleaned and disinfected with 70% ethanol.

Cell Preparation of the CC531 Cells for the Tumor Inoculation:

The RPMI medium is aspirated from the cell culture flask and the cell sheet is briefly washed with 3 to 4 mL of trypsin solution. After that, 1 mL (25 cc cell culture flask) or 1.5 mL (75 cc cell culture flask) of trypsin solution is added to the cells and incubated for 10 minutes in the incubator. After that, the flask is taken out and the contents are taken up in 5 mL (25 cc cell culture flask) or 10 mL (75 cc cell culture flask) of RPMI medium. For counting the vital cells, 50 μl of the cell suspension are stained with 50 mL of Trypan blue (alive-dead staining). Because of the increased cell permeability, the dead cells stain blue. Only the vital cells are counted in the Neubauer counting chamber and the count is converted to a figure, equivalent to the total volume.

The cell suspension is washed twice at 800 to 1000 rpm for 3 to 5 minutes with phosphate-buffered saline (PBS) and then made up to volume with the required amount of PBS ($3 \times 10^5$/100 μl of PBS per animal).

Inoculation of the CC531 Cells:

The anesthetized rats are opened up in the Linea alba, caudally of the xyphoid. Subsequently, the left liver lobe is advanced. For this purpose, a sterile gauze bandage (5 cm×5 cm) is used, which is soaked in 0.9% sodium chloride solution, in that the liver lobe is carefully taken hold of with the gauze and pulled out about 3 to 4 cm. The advanced portion of the liver is placed on the abdominal wall on moist gauze compresses. The freshly prepared cell suspension ($3 \times 10^5$ vital tumor cells in 100 μl of PBS per animal) is injected slowly over a sub-capsular puncture into the left liver lobe (needle: 27 G×¼", No. 20, 0.4×20 mm, TERMUO, Madrid). As the needle is being pulled out, the puncture site is compressed with a cotton swab, in order to prevent the cell suspension flowing away. The puncture opening is then closed off with a drop of tissue adhesive (Histoacryl®, B. Braun Surgical GmbH, Meslungen) and the swab can be removed. The liver lobe is replaced carefully in the abdominal cavity and the abdomen is sutured. Ten to fourteen days after the tumor inoculation, a palpable (approximately 1 cc) tumor has grown in the liver.

Intraarterial Application of the DNA/Liposome Complexes:

The abdomen of the anesthetized rats is opened about 5 to 6 cm parallel to the costal arch caudally of the xyphoid. With the help of moistened gauze compresses, the liver portions are displaced cranially and the intestinal portions caudally, so that the lower regions can be observed without hindrance. The further steps take place under microsurgical conditions.

Looking through a microscope with 5× to 8× magnification, the *A. communis* (*A. hepatica*), *A. gastroduodenalis* and *A. hepatica* are exposed. See FIG. 2.

A silk thread bridle (5/0, 1 metric, Perma-Hand® silk, braided, ETHICON, Norderstedt) is placed around the *A. hepatica propria* and the *A. gastroduodenalis* is ligated distally. Close to the exit of the *A. communis*, a thread with a loosened knot is placed around the *A. gastroduodenalis* and subsequently arteriotomized proximally to the ligature. A catheter is introduced carefully through this opening into the vessel and pushed further intravasally. The catheter tube, so placed, is fixed once with the knot previously prepared. Over a hypodermic needle at the other end of the tube, Ringer solution (B. Braun Meslungen AG, Meslungen) is injected (approximately 0.2 mL) under visual control, in order to control the correct discharge of the liquid and the catheter seat in the vessel. After that, the liposomes/DNA complexes are applied (with DCES), alternating with 50 µl of liposomes and 30 seconds of blood flow through the *A. communis* (loosening the bridled vessel). After the injection is completed, the catheter tube is rinsed once again with Ringer solution (0.2 to 0.3 mL) and pulled out of the vessel. With the previously placed knot, the *A. gastroduodenalis* can then be tied off proximal to the opening. After that, the gauze compresses are removed and the rats are taken care of further.

Treatment of the Rats with Ganciclovir:

Five days after the intraarterial administration of the liposomes/DNA complex, the rats are treated for 14 days with ganciclovir sodium (Cymeven® i.v., Hoffman-La Roche, Grenzach-Wyhlen). For this purpose, 100 mg per kg of body weight of ganciclovir is administered intraperitonally to the animals once daily. For this purpose, the rats were held by the neck with one hand and lifted out of the cage. After an examining aspiration, the rats are injected slowly in the abdomen in the region of the middle line using a 1 mL syringe with a sterile needle (27 G×¾", No. 20, 0.4×20 mm, TERMUO, Madrid).

Killing the Experimental Animals and Sampling the Blood:

On the day, on which they are killed, the rats are anesthetized and, after complete analgesia and anesthesia have set in, punctured with a 1 mm syringe (Omnifix®-F, disposable syringe, B. Braun Melsungen AG, Melsungen). For this purpose, the individual animal is placed on its back and, at the level of an imaginary line connecting the two elbows, punctured in the thorax so that the needle (25 G×⅝, 0.5×16 mm) is guided to the right of the sternum in the craniodorsal direction. The heart is punctured until the animal dies (approximately 4-6 mL of whole blood).

The blood obtained is kept for 1 to 2 hours at room temperature or overnight at 4° C. The coagulant formed is then carefully detached from the wall of the tube and centrifuged for 5 minutes at a maximum of 3000 rpm. The supernatant (serum) is then carefully siphoned off and, if necessary, centrifuged once again in order to eliminate admixed erythrocytes. The serum, so obtained, is then deep frozen and kept at −20° C.

Organ Removal and Preparation:

The abdomen and thorax of the dead rats are opened and the organs required (liver tumor, liver, kidneys, pancreas, spleen, heart, lung, lymph nodes (from the intestinal mesentery and the axilla)) are removed. All organs are deep frozen at −40° C. with 2-methylbutane (Roth, Karlsruhe) as refrigerant and stored at −70° C.

Determination of the Size of the Tumor:

The tumor size is determined using the formula $V = a \times b^2 / 2$, in which a is the largest and b the smallest extent of the tumor. The tumor diameters are measured twice for each animal (day 10 and day 30).

Serum Analysis:

The serum samples obtained are analyzed with the Vet Test 8008 (IDEXX GmbH, Wörrstadt, Germany) analytical instrument for veterinary medicine for 16 different blood parameters (photometric measurement), which involved the following substances and enzymes:

| Substrates | Intracellular Enzymes | Excretory Enzymes |
|---|---|---|
| Albumin (g/dl) | Creatinine kinase (mg/dl) | α-Amylase (IU) |
| Total bilirubin (mg/dl) | Aspartate amino transferase (IU) | Lipase (IU) |
| Cholesterol (mg/dl) | Alanine amino transferase (IU) | |
| Creatinine (mg/dl) | Lactate dehydrogenase (IU) | |
| BUN (urea) (mg/dl) | Alkaline phosphatase (IU) | |
| Glucose (mg/dl) | γ-Glutamyl transferase (IU) | |
| Ammonia (mg/dl) | | |

Preparation of Frozen Section:

Frozen sections, 8 to 12 µm thick, were prepared from the deep-frozen organs (liver, liver tumor, lung, kidneys, pancreas) using a cryotome (Kryostat of LEICA Instruments GMbH; Nuβloch). The sections were placed on glass microscope slides coated with poly-L-lysine and dried at room temperature. The sections are fixed for 5 minutes in 2% paraformaldehyde solution at 4° C. or for 5 minutes in ice-cold acetone, depending on the further use. The sections are then air dried and stored at −20° C. or stained immediately afterwards.

Histological Evaluation

Hemalum-Eosin Staining (Survey Staining):

For the histological survey preparations, a double staining with hemalum-eosin is prepared. Basophilic cell structures are stained blue (selective blue staining of the nucleus) by hemalum using the method of Mayer. The plasma is dyed red with the aniline dye eosin Y.

X-Gal Staining:

In order to localize the transfected cells and to evaluate the transfer efficiency attained after application of the liposomal pUT651 plasmid, the frozen sections prepared are stained in the following way. The frozen sections, fixed with paraformaldehyde, are washed twice for 5 to 10 minutes in PBS at room temperature and transferred immediately into the freshly prepared incubation solution* and incubated for 4 to 24 hours at 37° C. (development of the blue staining). Subsequently, the sections are rinsed briefly in distilled water and incubated for 30 seconds to 1 minute in eosin. The sections are then dewatered over the increasing alcohol series up to xylene and sealed with Eukitt®.

*X-Gal Incubation Solution:

for 80 mL=84 mL 1.1 mM $MgCl_2$ (22.36 mg in 100 mL of PBS (pH 7.2)
   6 mL of 50 mM $K_3[Fe(CN)_6]$ (1.645 g in 100 mL of $H_2O$)
   6 mL of 50 mM $K_4[Fe(CN)_6]$ (2.112 g in 100 mL of $H_2O$)
   2.1 mL of 20 mg/mL X-Gal in N,N-dimethylformamide Experimental Procedure:

| | | |
|---|---|---|
| Day 0 | Tumor inoculation | $3 \times 10^5$ vital CC531 cells in 100 µl of PBS are injected subcapsular into the liver |
| 10 to 14 days later | | A solid 1 cc tumor has grown in the liver |

-continued

| Day 10 | Intraarterial OP | The liposomal DCES with the suicide gene is administered over the liver artery |
| Day 15 | Ganciclovir administered | Start with the GCV administration (i.p.) 100 mg per kg of body weight once daily for 14 days |
| Day 30 | Killing | with intracardial blood withdrawal |

Reporter Gene Transfer:

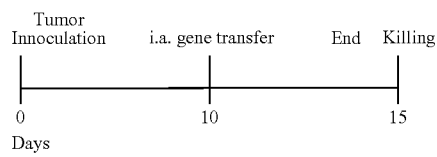

Suicide Gene Transfer:

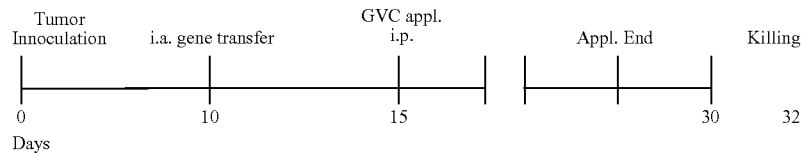

Results:

| Example | Plasmid | Liposomes | Embolisate | Dilution |
|---|---|---|---|---|
| 1 | 10 µg pUT651 | 50 µl MLV-PEG | 100 µl Spherex ® | 250 µl Ringer solution |
| 2 | 10 µg pUT649 | 50 µl MLV-PEG | 100 µl Spherex ® | 250 µl Ringer solution |
| 3 | 20 µg pUT649 | 50 µl MLV-PEG | 100 µl Spherex ® | 250 µl Ringer solution |
| 4 | 10 µg pBS-tk | 50 µl MLV-PEG | 100 µl Spherex ® | 250 µl Ringer solution |
| Control | without | without | without | 250 µl Ringer solution |

EXAMPLE 1

(10 µg) is administered to the tumor-carrying rats with the DCES on day 10. Five days later, the expected transfection of the lacZ reporter gene construct is strongest around the tumor and the animals are killed. Subsequently, the organs are removed and worked up as described above. Frozen sections, 12 µm thick, are prepared, fixed with 2% paraformaldehyde solution, washed and incubated at 37° C. overnight in a prepared X-Gal solution. The blue β-galactosidase colored complex can be seen clearly in the region of the edge seam of the tumor. This means that DNA can be transfected selectively with this system in the sensitive growth zone of the tumor. As a rule, no other organs are affected.

EXAMPLE 2 pUT649 (10 mg) is administered to the tumor-carrying rats with the DCES on day 10. The tumor size is measured during the operation. Five days later, the expected transfection of the suicide gene construct is strongest around the tumor and the GCV administration to the animals is commenced (once daily, 100 mg/kg of body weight). On day 30, the animals are killed. Subsequently, the tumor is measured and blood and organs are removed and worked up as described above. Frozen sections, 12 µm thick, are prepared, fixed with 2% paraformaldehyde solution, washed and stained with the hematoxalyn-eosin stain. The evaluation showed a statistically significant decrease in the liver metastases in comparison to the control group. Complete tumor regression cannot be detected.

(See Diagram in Appendix)

EXAMPLE 3 pUT649 (20 mg) is administered to the tumor-carrying rats with the DCES on day 10. The tumor size is measured during the operation. Five days later, the expected transfection of the suicide gene construct is strongest around the tumor and the GCV administration to the animals is commenced (once daily, 100 mg/kg of body weight). On day 30, the animals are killed. Subsequently, the tumor is measured and blood and organs are removed and worked up as described above. Frozen sections, 12 µm thick, are prepared, fixed with 2% paraformaldehyde solution, washed and stained with the hematoxalyn-eosin stain. The evaluation shows a statistically significant decrease in the liver metastases in comparison to the control group. Complete tumor regression cannot be detected.

(See Diagram in Appendix)

EXAMPLE 4 pBS-tk (10 mg) is administered to the tumor-carrying rats with the DCES on day 10. The tumor size is measured during the operation. Five days later, the expected transfection of the suicide gene construct is strongest around the tumor and the GCV administration to the animals is commenced (once daily, 100 mg/kg of body weight). On day 30, the animals are killed. Subsequently, the tumor is measured and blood and organs are removed and worked up as described above. Frozen sections, 12 µm thick, are prepared, fixed with 2% paraformaldehyde solution, washed and stained with the hematoxalyn-eosin stain. The evaluation showed that, because of the weaker promoter, a statistically significant decrease in the liver metastases in comparison to the control group, cannot be attained.

(See Diagram in Appendix)

ABBREVIATIONS

CEA Promoter of the carcino-embryonic antigen

CMV Promoter of the cytomegalo virus

DCES Drug carrier embolisates system

HSV-tk Herpes simplex virus thymidine kinase i.a. Intraarterial i.p. Intraperitoneal KGW Body weight lacZ gene Reporter gene, codes the β-galactosidase MLV PEG Multilamellar vesicles of polyethylene glycol OP Operation

What is claimed is:

1. A composition suitable for effecting gene transfer, consisting of:
   (a) one or more genetic materials chosen from the group consisting of DNA and RNA,
   (b) liposomes consisting of (1) PEG, (2) a steroid, (3) a charged lipid component, (4) genetic material and (5) a carrier liquid,
   (c) one or more polymer particles selected from the group consisting of nanoparticles, starch particles, gelatin, and Poloxamer,
   (d) contrasting agent selected from the group consisting of iodine-, gadolinium-, magnetite- and fluorine-containing contrasting agent, and
   (e) at least one component that assists in packing DNA more tightly.

2. The composition of claim 1, wherein the component that assists in packing DNA more tightly is selected from the group consisting of nuclear capsid protein NCP 7, HMG, polyethylene imine, poly-L-lysine and protamine sulfate.

3. The composition of claim 1, wherein the genetic material encodes one or more proteins selected from the group consisting of herpes simplex-virus thymidine kinase gene (HSVtk), deaminase, NR/CB 1954, purine nucleoside phosphorylase and cytokine genes.

4. The composition of claim 1, wherein the genetic material encodes at least one interleukin (IL) selected from the group consisting of IL-2, IL-4, IL-6, IL-10, L-12 and IL-15.

5. The composition of claim 1, wherein the molar ratio of amphiphile to steroid to charged lipid component is 1:0.3:0.1.

6. The composition of claim 1, wherein the molar ratio of amphiphile to steroid to charged lipid component is 1:1:0.1.

7. The composition of claim 1, wherein the molar ratio of amphiphile to steroid to charged lipid component is or 1:1:0.5.

8. The composition of claim 1, wherein the molar ratio of charged lipid component to contrasting agent is from 2:1 to 10:1.

9. The composition of claim 1, wherein the steroid is chosen from the group consisting of cholesterol, diethoxycholesterol and sitosterol.

10. The composition of claim 1, wherein the charged lipid component is an anion of a lipid selected from the group consisting of diacetyl phosphate, palmitic acid, stearic acid, a phospholipid, and a sphingolipid.

11. The composition of claim 10, wherein the charged lipid component is fluorinated.

12. The composition of claim 1, wherein the polymer particles consist of a 25% aqueous solution of Poloxamer.

13. The composition of claim 1, wherein the liposomes are present in at least one form selected from the group consisting of SUV (small unilamellar vesicles), LUV (large unilamellar vesicles), REV (reverse phase evaporation vesicles), MLV (multilamellar vesicles), and 3β N-(N,N'-dimethylaminoethane)-carbamoyl cholesterol (DAC-chol) liposomes.

14. The composition of claim 1, wherein the polymer particles consist of starch particles having an average diameter of 40 μm to 90 μm.

15. The composition of claim 14, wherein the starch particles have a particle size of 60 μm to 90 μm.

16. The composition of claim 14, wherein the starch particles have a concentration of from 5 mg/ml to 70 mg/ml upon resuspending the composition in water or aqueous buffer.

17. The composition of claim 1, wherein the polymer particles consist of gelatin.

18. The composition of claim 1, wherein the contrasting agent consist of phenyl derivatives having one or more iodine substituents.

19. The composition of claim 18, wherein the contrasting agent is selected from the group consisting of Iopromide, Ioxitalamate, Ioxagate, Iopamidol, Iohexyl, Iotralon, and Metrizamide.

20. The composition of claim 1, wherein the fluorine-containing contrasting agents consist of fluorinated lipids.

21. The composition of claim 1, consisting of
   (a) a LacZ gene and a HSVtk gene,
   (b) MLV PEG liposomes,
   (c) starch particles and
   (d) the contrasting composition is fluorinated.

22. The composition of claim 1, wherein the genetic material is encapsulated in MLV PEG, and the polymer particles are starch particles.

23. The composition of claim 1, wherein the polymer particles are lyophilized starch particles.

24. The composition of claim 1, wherein the polymer particles are degradable starch particles.

25. The composition of claim 1, comprising 30 mg to 90 mg of starch particles and 5 mg to 100 mg of genetic material.

26. The composition of claim 1, wherein the polymer particles are nanoparticles.

27. The composition of claim 10, wherein the phospholipid is chosen from the group consisting of phosphatidyl serine and phosphatid acid; the sphingolipid is sulfatide; and the PEG is MPEG.

28. A composition suitable for effective gene transfer consisting of:
   (a) one or more genetic materials chosen from the group consisting of DNA and RNA;
   (b) liposomes consisting of (1) PEG, (2) steroid, (3) a charged lipid component, (4) genetic material, and (5) a carrier liquid;
   (c) one or more polymer particles selected from the group consisting of nanoparticles, starch particles, gelatin and Poloxamer;
   (d) a contrasting agent selected from the group consisting of iodine-, gadolinium-, magnetite-, and fluorine-containing contrasting agents;
   (e) at least one component that assists in packing DNA more tightly; and
   (f) anti-Ki-67-immune PEG liposomes or anti-CEA PEG liposomes,
   wherein the liposomes are present in at least one form selected from the group consisting of small unilamellar vesicles (SUV), large unilamellar vesicles (LUV), reverse phase evaporation vesicles (REV, mulitlumellar vesicles (MLV) and 3βN-(N,N'-dimethylaminoethane)-carbamoyl cholesterol (DAC-chol) liposomes.

* * * * *